US00PP37097P2

(12) United States Plant Patent
Lim

(10) Patent No.: US PP37,097 P2
(45) Date of Patent: Nov. 18, 2025

(54) FLORIBUNDA SHRUB ROSE NAMED 'ALTsky'

(50) Latin Name: *Rosa hybrida*
Varietal Denomination: ALTsky

(71) Applicant: Altman Specialty Plants llc, Vista, CA (US)

(72) Inventor: Peter Lim, Escondido, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/022,478

(22) Filed: Jan. 15, 2025

(51) Int. Cl.
*A01H 5/02* (2018.01)
*A01H 6/74* (2018.01)

(52) U.S. Cl.
USPC ..... Plt./149

(58) Field of Classification Search
USPC ..... Plt./101, 141, 149
See application file for complete search history.

(56) References Cited

U.S. PATENT DOCUMENTS

PP16,198 P2 * 1/2006 Swane ..... Plt./149

* cited by examiner

*Primary Examiner* — Susan McCormick Ewoldt

(57) ABSTRACT

A new and distinct cultivar of Rose plant named 'ALTsky' is disclosed, characterized by distinctive semi-double flowers dark pink flowers with an average of 15 petals. The new cultivar is a low-growing shrub rose which blooms prolifically. Plants have dark, foliage resistant to black spot and powdery mildew disease. The new variety is normally produced as an outdoor garden or container plant.

1 Drawing Sheet

Latin name of the genus and species: *Rosa hybrida.*
Variety denomination: 'ALTsky'.

BACKGROUND OF THE INVENTION

The new *Rosa* cultivar is a product of a planned breeding program conducted by the inventor, Peter Lim. The objective of the breeding program was to produce vigorous new garden rose varieties with easy rooting for ornamental commercial applications. The cross resulting in this new variety was made Jun. 10, 2011.

The seed parent is *Rosa* 'WEKsmopur', U.S. Plant Pat. No. 18,850. The pollen parent is *Rosa* 'BAIsuhe' U.S. Plant Pat. No. 20,486. The new variety was selected in August of 2014 by the inventor in a group of seedlings resulting from the 2013 crossing, in a nursery in Vista, California.

Asexual reproduction of the new cultivar has been performed by vegetative cuttings. This was first performed at a research greenhouse in Vista, California in July of 2012 and has shown that the unique features of this cultivar are stable and reproduced true to type in successive generations.

SUMMARY OF THE INVENTION

The cultivar 'ALTsky' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTsky' These characteristics in combination distinguish 'ALTsky' as a new and distinct *Rosa* cultivar:

1. Low growing shrub rose.
2. Semi-double flower with an average of 15 petals.

3. Easy to root from cuttings.
4. Prolific blooming.
5. Dark glossy foliage resistant to black spot and powdery mildew disease.

PARENT COMPARISONS

Plants of the new cultivar 'ALTsky' are similar to plants of the seed parent, in most horticultural characteristics, however, plants of the new cultivar 'ALTsky' differ in the following:

1. Flowers of the new cultivar are a more red-purple color than the deep purple of the seed parent.
2. Flowers of the new cultivar have less petals than the seed parent.
3. Plants of the new cultivar are lower growing than plants of the seed parent.

Plants of the new cultivar 'ALTsky' are similar to plants of the pollen parent in most horticultural characteristics, however, plants of the new cultivar 'ALTsky' differs in the following;

1. Flowers of the new cultivar are a different red-purple color than the bright red/pink color of the pollen parent. Mature upper petal color of 'ALTsky' is Red-Purple 61B strongly flushed 61C; mature upper petal color of the pollen parent is Red-Purple N66A suffused N66C
2. Foliage of the new cultivar is glossier than foliage of the pollen parent.
3. Flowers of the new cultivar have less petals than flowers of the pollen parent.

COMMERCIAL COMPARISON

Plants of the new cultivar 'ALTsky' can be compared to the commercial variety *Rosa* 'Prose', U.S. Plant Pat. No.

16,198. These varieties are similar in most horticultural characteristics, however 'ALTsky' differs in the following:

1. Flowers of the new cultivar are a more red-purple color than the deep burgundy-purple of this comparator
2. Flowers of the new cultivar are smaller than flowers of this comparator.
3. Flowers of the new cultivar have less petals than flowers of this comparator.

Plants of the new cultivar 'ALTsky' can also be compared to the commercial variety *Rosa* 'WEKEBTIDERE', U.S. Plant Pat. No. 24,725. These varieties are similar in most horticultural characteristics, however 'ALTsky' differs in the following:

1. Flowers of the new cultivar are a more red-purple color than the deep burgundy-purple of this comparator
2. Flowers of the new cultivar are smaller than flowers of this comparator.
3. Flowers of the new cultivar have less petals than flowers of this comparator.
4. Plants of the new cultivar are much less upright than plants of this comparator.

BRIEF DESCRIPTION OF THE PHOTOGRAPH

The accompanying photograph illustrates in full color a close-up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2015 except where general terms of ordinary dictionary significance are used. The following observations and measurements describe 'ALTsky' plants grown outdoors, in Vista, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTsky'.

Market classification: Floribunda rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Semi-upright, outwardly spreading.

Container size: 2-gallon.

Height: 60 cm.

Plant spread: 55 cm.

Rootstock: Own root.

Growth rate: Rapid.

Branching characteristics: Sympodial branching.

Length of primary lateral branches: Average range 20 to 40 cm.

Diameter of lateral branches: Approximately 4 to 6 mm.

Quantity of branches: 4 to 5 main branches, moderate lateral branches, 4 to 8 lateral branches per main branch.

Branches:

Young wood:

*Diameter*.—Approximately 6 mm.

*Texture*.—Glabrous.

*Approximate density/quantity of prickles*.—Moderate.

*Color*.—Near RHS Green 137D.

Branches:

Old wood:

*Diameter*.—Approximately 8 to 16 mm.

*Color*.—Near RHS Green 137 streaked Greyed-Green195A.

*Texture*.—Glabrous. Oldest, basal growth scaly.

Thorns:

*Approximate density/quantity of thorns*.—Young growth: Very few to no thorns. Mature growth: Very few to no thorns.

FOLIAGE

Leaf:

*Arrangement*.—Alternate and compound.

*Quantity*.—Average 5 to 10 per main branch.

*Internode*.—Average range 2 to 3 cm.

*Average length*.—Approximately 9 cm.

*Average width*.—Approximately 6 cm.

Rachis:

*Average length*.—Approximately 4.5 cm.

*Average diameter*.—Approximately 2 mm.

*Color*.—Upper surface: Near RHS Green 137C. Lower surface: Near RHS Green 143C.

*Texture*.—Glabrous. No prickles.

Leaflet:

*Quantity*.—7 per leaf.

*Average length*.—Approximately 3.5 cm to 4 cm.

*Average width*.—Approximately 2.5 cm.

*Shape of blade*.—Broad ovate.

*Apex*.—Acute.

*Base*.—Broadly rounded.

*Margin*.—Finely serrate.

*Appearance of top surface*.—Very glossy.

*Appearance of bottom surface*.—Matte.

*Texture of top surface*.—Glabrous.

*Texture of bottom surface*.—Glabrous.

*Color*.—Young foliage upper side: Near RHS Green 137C. Young foliage under side: Near RHS Green 138B. Mature foliage upper side: Near RHS Green NN137A. Mature foliage under side: Near RHS Green 137D.

*Venation*.—Type: Reticulate. Venation color upper side: Near RHS Green 137C. Venation color under side: Near RHS Yellow-Green 145A.

Petiole:

*Average length*.—Approximately 2 cm.

*Average diameter*.—Approximately 3 mm.

*Texture*.—Glabrous.

*Color*.—Upper surface: Near RHS Green NN137D. Lower surface: Near RHS Green 143A.

*Petiole wing*.—Typically 15 mm long and 5 mm wide. Apex apiculate. Upper surface colored near RHS Green 138A, lower surface colored near Green 137D. Texture: Glabrous.

FLOWER

Natural flowering season: Spring until Autumn.

Inflorescence type and habit: Semi-double rotate flowers.

Rate of flower opening: Approximately 5 days from bud to fully opened flower.
Flower longevity on plant: About 7 days after fully opened.
Quantity of flowers: 30 to 40 fully opened flowers and buds.
Flower size:
*Diameter*.—Approximately 5 cm.
*Height*.—Approximately 3.5 cm.
Flower shape:
*From above*.—Round to very slightly irregular round.
*Profile of upper part of flower*.—Flat.
*Profile of lower part of flower*.—Flat to concave.
Peduncle:
*Length*.—3 cm.
*Diameter*.—4 mm.
*Color*.—Near RHS Green 138A.
Petals:
*Petal arrangement*.—3 or 4 overlapping whorls.
*Petal quantity*.—Average 15.
*Length*.—3 cm.
*Width*.—2.5 cm.
*Shape*.—Broad deltate.
*Margin*.—Entire. Moderately ruffled
*Apex*.—Rounded with 5 to 7 irregular shallow notches.
*Base*.—Very broad attenuate.
*Texture*.—Glabrous all surfaces.
*Color*.—When opening: Upper surface: Near RHS Red-Purple 61B. Lower surface: Near RHS Red-Purple 61B. Fully opened: Upper surface: Near RHS Red-Purple 61B strongly flushed 61C. Small basal blotch 69D. Lower surface: Near RHS Red-Purple 61B strongly flushed 61C.
Bud:
*Shape*.—Ovate.
*Length*.—Approximately 3 cm.
*Diameter*.—Approximately 2 cm.
*Color*.—Near RHS Red-Purple 61B.
Sepals:
*Quantity*.—5.
*Length*.—2 cm.
*Width*.—10 mm.
*Shape*.—Narrow deltoid.
*Apex*.—Apiculate. Weak sepal extensions.
*Margin*.—Entire.
*Texture*.—Slightly pubescent lower surface, densely and softly pubescent upper surface.
*Color*.—Interior Surface: Near RHS Green 138B. Exterior Surface: Near RHS Green 138A.
Receptacle:
*Depth*.—4 mm.
*Diameter*.—6 mm.
*Shape*.—Flat.
*Color*.—Near RHS Yellow-Green 145D.

REPRODUCTIVE ORGANS

Stamens:
*Quantity*.—About 40 to 50.
*Filament length*.—8 mm to 11 mm.
*Filament color*.—Near RHS White 155D.
Anthers:
*Length*.—2 mm.
*Shape*.—Oblate.
*Color*.—Near RHS Yellow-Orange 17C.
*Pollen*.—None observed.
Pistil: Misshapen 3-parted structure in center of receptacle. About 9 mm in length and 4 mm in diameter. Colored near RHS Greyed-Yellow 161A.

OTHER CHARACTERISTICS

Seeds and fruits: Not observed.
Disease/pest resistance: Good overall disease resistance to normal pests and diseases typical of garden roses. Very good resistance to blackspot (*Diplocarpon rosae*) and powdery mildew (*Podosphaera pannosa*) disease.

What is claimed is:

1. A new and distinct cultivar of Rose plant named 'ALTsky' as herein illustrated and described.

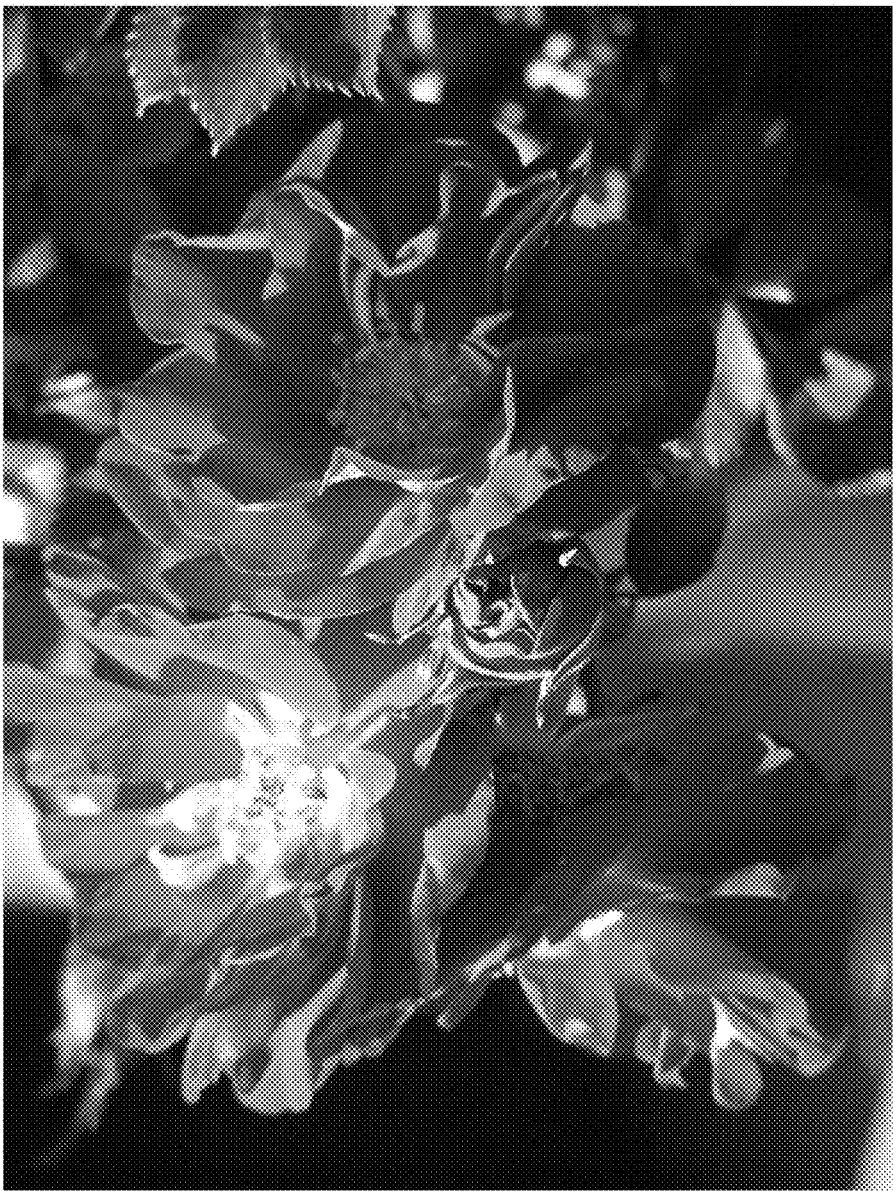

* * * * *